United States Patent [19]

Rey et al.

[11] Patent Number: 4,883,507
[45] Date of Patent: Nov. 28, 1989

[54] FILTER COMPRISING A MATERIAL OBTAINED BY FREEZE-DRYING, METHOD OF PREPARATION AND USE ESPECIALLY IN PHARMACY

[75] Inventors: Louis Rey, Epalinges, Switzerland; Brynjulf Ottar, Kjeller, Norway; Louis Lafon, Paris, France

[73] Assignee: Laboratoire L. Lafon, Paris, France

[21] Appl. No.: 213,308

[22] Filed: Jun. 29, 1988

[30] Foreign Application Priority Data

Jul. 8, 1987 [FR] France .............................. 87 09696
Aug. 12, 1987 [FR] France .............................. 87 11468
Sep. 4, 1987 [FR] France .............................. 87 12277

[51] Int. Cl.$^4$ .......................................... B01D 46/10
[52] U.S. Cl. .............................................. 55/97; 34/5; 55/502; 55/503; 55/523; 55/526; 55/528; 55/DIG. 5
[58] Field of Search ............... 34/5, 13; 55/502, 503, 55/523, 525-528, DIG. 5, 97; 210/510.1

[56] References Cited

U.S. PATENT DOCUMENTS

| 622,217 | 4/1899 | Fuller et al. ........................ 55/503 X |
| 3,428,584 | 2/1969 | Riley ...................................... 34/5 X |
| 3,782,083 | 1/1974 | Rosenberg ......................... 55/502 X |
| 3,855,712 | 12/1974 | Blonde .................................... 34/5 |
| 3,939,260 | 2/1976 | Lafon ...................................... 34/5 X |
| 4,148,732 | 4/1979 | Burrow et al. .................... 55/503 X |
| 4,155,247 | 5/1979 | Kaczmarek et al. ............. 55/503 X |
| 4,178,695 | 12/1979 | Erbeia ...................................... 34/5 |
| 4,305,502 | 12/1981 | Gregory et al. ...................... 34/5 X |
| 4,362,047 | 12/1982 | von Reis et al. ................. 55/503 X |
| 4,404,006 | 9/1983 | Williams et al. ............... 55/DIG. 5 |
| 4,416,777 | 11/1983 | Kuroda et al. ..................... 55/527 X |
| 4,490,407 | 12/1984 | Lafon ..................................... 34/5 X |
| 4,616,047 | 10/1986 | Lafon ..................................... 34/5 X |

FOREIGN PATENT DOCUMENTS

| 0064967 | 11/1982 | European Pat. Off. . |
| 1566272 | 1/1968 | France . |
| 25839 | 7/1978 | Japan ..................................... 55/16 |
| 1328641 | 8/1973 | United Kingdom . |

OTHER PUBLICATIONS

EXPERIENTA, vol. XXI, fasc. 5, 1965, pp. 241–304; L. Rey.

Primary Examiner—Robert Spitzer
Attorney, Agent, or Firm—Wegner & Bretschneider

[57] ABSTRACT

The present invention relates, by way of a novel industrial product, to a filter for gaseous fluid, which contains a lyophilized and compressed filter element in the form of a porous layer.

24 Claims, 1 Drawing Sheet

FIG_1      FIG_2

FIG_3

FILTER COMPRISING A MATERIAL OBTAINED BY FREEZE-DRYING, METHOD OF PREPARATION AND USE ESPECIALLY IN PHARMACY

FIELD OF THE INVENTION

The present invention concerns the field of filtration. It relates more particularly to (i) a filter containing a filter element or means obtained by freeze-drying or lyophilization and then compression, (ii) the method for the preparation of this filter and the said filter element, and (iii) the use of the said filter and the said filler element on the one hand in the field of the selective retention of gaseous or particulate products for purposes of separation, analysis and/or preparation, and on the other hand in the field of pharmaceutical forms comprising the said filter element as the matrix, in association with microparticles of active principle.

PRIOR ART

It is known that, in the field of filtration, filters made of cellulose, polyurethane, sintered metal, sintered glass, carbon etc. have already been used in the past. Now, these filters are found to have the disadvantage of not allowing complete recovery of the retained products, in particular because of the adsorption, retention and release or desorption capacities of the said filters. In particular, if the adsorption of a product on a filter involves strong binding forces, the washing of this filter may be incomplete when it is desired to recover the said product which has been retained. Such a case arises when the teaching of European patent application No. A-0 064 967 is followed, whereby submicron particles with a diameter of less than 600 nm are prepared by the polymerization of an alkyl cyanoacrylate to a polyalkyl cyanoacrylate in an aqueous medium containing a biologically active substance, and the insoluble particles of polyalkyl acrylate coated with the said biologically active substance are then collected by filtration on sintered glass.

Among the solutions known in the field of the filtration of liquid or gaseous fluids for retaining very fine asbestos fibers or submicron particles, it is known that filter membranes of microporous structure have already been used, especially so-called MILLIPORE ® membranes marketed by MILLIPORE S.A. of Saint-Quentin-en-Yvelines, and analogous membranes originating from other manufacturers. These microporous filter membranes are generally polymeric organic substances and in particular a cellulose ester (especially a cellulose acetate), a polyacrylate or polyacrylic material, polyvinylidene fluoride, polyethylene tetrafluoride, polyethylene, polypropylene or mixtures thereof. Furthermore, for analysis of the retained material, the said membranes are generally carbonized, so their use is generally limited to the filtration of inorganic particles and fibers which are not affected by carbonization.

French patent application No. A-1 566 272 has furthermore disclosed a dry membrane for the separation, by diffusion, of a particular gas (for example helium) from a mixture of gases containing this particular gas (for example so-called natural gas containing about 2 mol % of helium, 25 mol % of nitrogen and 66 mol % of methane, the remainder being made up of ethane, propane and various higher hydrocarbons), this membrane, which is insoluble in water, consisting of two layers: a first, porous layer made of cellulose acetate, with a thickness $t_1$ (of the order of 10 to 100 $\mu$m), and a second, non-porous layer made of cellulose acetate, with a smaller thickness $t_2$ (of the order of 0.1 to 1 $\mu$m), which is obtained by knife-coating onto a temporary support, drying and then lyophilization of the resulting film. French patent application No. A-1 566 272 does not teach the preparation of a porous material obtained by lyophilization followed by compaction according to the invention, which is useful as a filter element.

There is a need for a filter material which is soluble in water or another customary organic or inorganic solvent and which is suitable for retaining submicron particles. In actual fact, although the special water-soluble laboratory filters made in particular of non-woven cellulosic material are relatively satisfactory from the analytical point of view in the field of the filtration of macroscopic products, they are not suitable for the separation of particles of small dimensions, such as submicron particles, conveyed by gaseous fluids.

There is also a need for micron-size particles and, preferably, submicron-size particles for use in therapy or cosmetics.

In particular, it is seriously believed that with submicron particles, enzymatic degradation, in particular, might be avoided and that certain compounds not possessing transporters in the cell membranes might nevertheless be administered to the organism through incorporation by purely physical processes comparable to pinocytosis.

The pilot-scale and, a fortiori, industrial-scale production of submicron particles is a difficult operation if one takes into account the fact that, in gaseous suspension, they only undergo molecular agitation movements, or Brownian motion, and are therefore very difficult to collect and concentrate. Moreover it should be added that, in an aerosol, most of the particles are very aggressive towards the organism, their entry into the respiratory tract being capable of causing catastrophic physiological reactions in some cases and even of exhibiting a very high toxicity, which is the more acute the smaller the particle size.

Attempts are therefore being made to prepare submicron-size particles by means of an appropriate technology which is perfectly reliable and reproducible and which makes it possible to overcome the above-mentioned difficulties relating to microparticles, such as submicron-size particles in particular, especially for the purpose of improving the efficacy and/or the bioavailability of the active ingredients of which the said submicron particles consist.

SUBJECT OF THE INVENTION

According to the invention, a novel technical solution is proposed for solving the problem of the filtration of gaseous fluids in order to retain gaseous products of fine particles for purposes of separation, analysis and/or preparation.

This novel technical solution involves the use of a freeze-dried or lyophilized and compressed material as a porous filter element. It is based on the fact that freeze-drying or lyophilization (i.e. cold-drying, an operation which involves freezing of a preparation containing a solvating, diluting or dispersing liquid, in particular at a temperature of $-40°$ C. and/or $-80°$ C., followed by evaporation of the said frozen liquid by vacuum sublimation) leads to porous products which have a relatively large specific surface area (expressed in particular in $cm^2/cm^3$) and which are capable of retaining their porous texture until they are brought into contact with one of their solvents.

According to one aspect of the invention, it is proposed to provide a novel filter material which is relatively simple to prepare and which is intended for use in the field of the filtration of gaseous fluids for the purpose of retaining essentially the majority of the fine particles which they contain, especially when aerosols are involved.

According to another aspect of the invention, a filter material is proposed which contains, in its bulk, at least one reagent for fixing and/or determining the gaseous substances contained as impurities or components of the said gaseous fluids.

According to yet another aspect of the invention, a filter material is proposed which is soluble in a customary organic or inorganic solvent, advantageously water, for the purpose of recovering the retained substances (especially submicron particles which are insoluble in the said solvent) and/or determining the said substances. Conversely, another filter material is proposed which is insoluble in the selective solvent for the retained substance, for the purpose of determining the latter.

According to another aspect of the invention, a method is proposed for the preparation of a filter for gaseous fluids and of the filter element of the said filter.

According to yet another aspect of the invention, it is proposed to prepare a pharmaceutical form comprising at least one water-soluble or water-dispersible active ingredient.

According to another aspect of the invention, it is proposed to prepare a pharmaceutical form comprising at least one active ingredient (which in particular is soluble in a customary solvent and insoluble in the other conventional solvents) in the form of coated microparticles.

According to yet another aspect of the invention, a method is proposed for the preparation of the above-mentioned pharmaceutical forms, which is useful especially for isolating the said microparticles and in particular those which have been coated.

DETAILED DESCRIPTION OF THE INVENTION

According to the invention, a novel filter for gaseous fluid is proposed which is particularly suitable for retaining the particles contained in or conveyed by the said gaseous fluid which have a size less than or equal to 5 $\mu$m and in particular less than or equal to 2.5 $\mu$m, and especially the particles which have a size less than or equal to 1 $\mu$m and preferably a size of between 1 and 0.01 $\mu$m, and/or gaseous products contained in the said gaseous fluid which can be purified. This filter contains a lyophilized and compressed filter element in the form of a porous layer.

The term "freeze-drying" or "lyophilization" is understood here as meaning any method of cold-drying, which involves the freezing of a liquid or pasty preparation followed by the removal or evaporation, by sublimation, of the solvating, diluting and/or dispersing liquid used to produce the said preparation, in the manner indicated above, whatever the said liquid may be.

More precisely, the filter according to the invention contains a filter element in the form of a porous layer, which consists of a solid material obtained in the dry state by (i) freezing, (ii) freeze-drying and then (iii) compression in order to give it sufficient mechanical strength essentially to prevent it from cracking when the gaseous fluid passes through it.

The compression step, which is carried out to improve the mechanical strength of the solid filter material when the gaseous fluid passes through it, constitutes a kind of sintering process which produces a porous structure resulting from the porous structure obtained by expansion during freeze-drying.

According to one characteristic of the invention, the filter element consists of a solid material which has been compressed, after freeze-drying, in a compression ratio of between about 1.1 and about 5. Advantageously, the said compression ratio will be between 1.2 and 4 and preferably between 1.25 and 3.60.

In a modified embodiment, the filter element which is in the form of a porous layer consists of a solid material obtained in the dry state by (a) freezing, (b) grinding, (c) freeze-drying and then (d) compression.

To avoid practically all cracking of the filter element during the passage of the gaseous fluid which it is desired to filter, it is recommended to incorporate a appropriate cohesive agent into the bulk of the solid material forming the said filter element. The said cohesive agent can be selected especially from the group comprising plasticizing substances. As a modified embodiment, the plasticizing cohesive agent can be an organic filler, especially a polymer, which can be expanded by lyophilization and which possesses plasticizing properties. Examples of plasticizing fillers according to the invention which may be mentioned in particular are hydroxypropyl methyl cellulose, polyvinyl alcohol and powdered milk.

In a preferred embodiment, the concentration of the plasticizing cohesive agent present in the bulk of the solid material of the filter element is between 1% and 75% by weight, relative to the total weight of the said solid material.

The solid material which forms the filter element of the filter according to the invention comprises essentially one or more inert inorganic or organic fillers which do not react with the gaseous fluids to be filtered. Among the suitable fillers, there may be mentioned, in particular, glass, ceramic, silica, carbon, cellulosic derivatives, resins and organic polymers, especially polyacrylic, polymethacrylic, polyvinylpyrrolidone, polystyrene and polyurethane materials and mixtures thereof. These fillers can be in the form of granules, particles or fibers. Of course, mixtures of particles and fibers give the filter element a better cohesion with respect to cracking, the fibers then acting as both filler and means of cohesion.

Among the inorganic fillers, it is thus possible to use glass fibers, ceramic fibers, expanded carbon particles and silica. Particles of metals, metal salts and metal oxides can also be used where the substances are inert towards the gaseous fluids to be filtered, since, as illustrated below, the said substances can be used as reagents, especially in the determination or detection of gaseous products contained in certain gaseous fluids.

Among the suitable organic fillers, it is possible to use the polymeric substances in the form of particles or fibers.

In general, the filler which will be lyophilized and compressed to form the bulk or matrix of the filter element is preferably essentially in the form of particles, if necessary with a small proportion of fibers for the cohesion of the said filter element.

According to an advantageous way of putting the invention into effect, the filter element consists of a solid material which is soluble or dispersible in a solvent selected from the group comprising water, inorganic solvents, organic solvents and mixtures thereof.

Appropriately, preference is given more particularly to the fillers which are soluble or microdispersible in water, namely: polysaccharide materials such as dextran, carboxymethyl cellulose and hydroxypropyl cellulose, monosaccharide or disaccharide materials such as glucose, lactose, maltose and sucrose, polyvinylic materials such as polyvinyl alcohol polyacrylic materials such as polyacrylate and polymethacrylate salts or esters, polyvinylpyrrolidones and mixtures thereof, especially the powdered milk mentioned above, which is a product containing, in particular, lactose, casein and other protein and polypeptide substances, and milk extracts. As a modified embodiment, it is possible to use a filler which is insoluble in water but soluble in an appropriate customary organic solvent.

The filter element according to the invention can also contain, in its bulk, one or more reagents, especially reagents for analyzing mixtures of gases.

It suffices, for example, to introduce a basic substance into the material of the filter element in order to retain the traces of acids in the mixture analyzed (especially sulfur oxides and nitrogen oxides, HCl vapors, etc.). Finely divided metals can also be introduced into the material, making it possible to measure the $CO/CO_2$ ratio by determination of the methane resulting from the catalytic conversion of the CO, using an electron capture detector.

The filter element according to the invention, which is obtained by freezing, grinding (to give granules with a size of the order of about 1 to 3 mm), freeze-drying and then compression, offers the advantage of being relatively light and, remarkably, of being able to be dissolved or dispersed easily in very small amounts of appropriate solvents after the gaseous fluid to be filtered has passed through.

The said lyophilized and compressed filter element is placed in the path of a circulating gaseous fluid containing, for example, micron-size or submicronsize particles, for example a sample of air taken from the atmosphere in regions of high urban or industrial pollution. A certain volume of air, corresponding to a given mass of gas under normal temperature and pressure conditions, and dehydrated, if appropriate, by passage through a denuder of selective adsorption or porosity, is passed through a layer of greater or lesser thickness of the said filter element. Because of the very high porosity of this material, the air circulates very easily therein with no appreciable loss of pressure. Furthermore, the very fine structure of the material is responsible for capturing the solid particulate constituents which may deposit thereon due to impact, Brownian motion or adsorption or as a result of electrostatic forces. In this respect, the lyophilized and compressed material according to the invention behaves like a high-efficiency filter.

The pressure loss, which depends especially on the thickness of the filter element, its compression ratio (the ratio of the thickness of the material before compression to the thickness of the said material after compression) and the resulting porosity, as well as on the pressure of the gaseous fluid to be filtered, is generally between 1 cm of $H_2O$ (about 98.06 Pa) and 100 cm of $H_2O$ (about 9806 Pa), i.e. more precisely between 2 cm of $H_2O$ (about 196.1 Pa) for an 8 mm thickness of filter material with a compression ratio of 1.25 and for a gaseous fluid with a flow rate of 300 1/min, relative to normal temperature and pressure conditions, and 76 cm of $H_2O$ (i.e. about 7452.5 Pa) for 14 mm thickness of filter material with a compression ratio of 3.6 and for a gaseous fluid with a flow rate of 4 1/min, relative to normal temperature and pressure conditions.

The material according to the invention, which forms the filter element, is perfectly suitable for the filtration of micron and submicron particles, i.e. particles with a size of between 5 and 0.01 $\mu$m, especially of between 2.5 and 0.01 $\mu$m and preferably of between 1 and 0.01 $\mu$m, conveyed by a gaseous fluid.

The lyophilization or freeze-drying involved in the preparation of this material is carried out by a method known per se, for example according to a technique described by L. R. REY et al., "Traitéde lyophilisation" ("Treatise on lyophilization"), published by Hermann, Paris 1961, pages 1–411; L. R. REY, Experientia 21, pages 241–246, (1965): L. R. REY, Proc. Roy. Soc. B, London 191, pages 9–19, (1975); U.S. patent application No. A-4 616 047; U.S. patent application No. A-4 178 695; British patent application No. A-1 328 641; U.S. patent application No. A-4 490 407 and U.S. patent application No. A-3 939 260.

According to the invention, the filter material is also useful for the preparation and separation of micron and, preferably, submicron particles of pharmaceutical active ingredients. These particles of active ingredients can be coated with a coating which is soluble or insoluble in water; among the water-insoluble coatings which are suitable, there may be mentioned the liposoluble coatings which are intended to disintegrate in the intestines.

The method for the preparation of the filter element according to the invention comprises freezing, at a temperature of −40° C. to −80° C., a liquid or pasty preparation of a polymeric substance and a solvating, diluting or dispersing liquid, grinding the resulting frozen solid product and freeze-drying the resulting ground product in order to sublime the solvating liquid, and then compressing the resulting freeze-dried product in a ratio of between 1.1 and 5.

A novel pharmaceutical form or composition is also proposed according to the invention, as a novel industrial product, the said pharmaceutical form comprising an association of (i) a physiologically acceptable matrix and (ii) at least one active ingredient in the form of particles, which is selected from therapeutic and cosmetic active principles; in this pharmaceutical form:

(A) the physiologically acceptable matrix is a porous solid material which has been obtained in the dry state by freezing, freeze-drying and compression in order to give the said material sufficient mechanical strength essentially to prevent it from cracking when a gaseous fluid passes through it; and (B) the active ingredient associated with the said matrix consists essentially of microparticles with a mean size of between 5 $\mu$m and 0.01 $\mu$m and is selected from substances which are (1) soluble in water, (2) insoluble in water or (3) coated.

The pharmaceutical form or composition referred to here is therefore one in which the active principle is in the form of microparticles and on the one hand is either soluble or insoluble in water, or on the other hand is coated, irrespective of its solubility in water.

A method for the preparation of such a pharmaceutical form or composition is also proposed, the said method comprising the following steps:

(1°) production of a preparation of the active ingredient in a liquid medium, the said active ingredient being either soluble or insoluble in the said liquid medium and its concentration in the said liquid medium being less than or equal to 10% (w/v);

(2°) nebulization of the resulting preparation to give an aerosol entrained in a stream of gaseous carrier fluid;

(3°) evaporation of the liquid medium of the aerosol so that the microparticles which result from drying of the said aerosol are conveyed by the said gaseous carrier fluid; and (4°) filtration of the said gaseous carrier fluid containing the active ingredient essentially in the form of microparticles, by means of a filter comprising, as the filter element, a porous solid material which has been obtained in the dry state by freezing, freeze-drying and compression in order to give the said material sufficient mechanical strength essentially to prevent it from cracking when a gaseous fluid passes through it for collection of the said microparticles on the filter element.

The pharmaceutical form or composition according to the invention, which is useful in therapy and in cosmetics, contains microparticles (which on the one hand are either soluble or insoluble in water, or on the other hand are coated, irrespective of its solubility in 1 water) with a mean size of between 5 μm and 0.01 μm. Of these particles, those which have a mean size less than or equal to 2.5 μm, in particular less than or equal to 1 μm, are preferred.

The matrix of the pharmaceutical form is obtained from the above-mentioned filter element. This filter element, which is presented in the form of a porous layer, consists of a solid material obtained in the dry state by (i) freezing, (ii) freeze-drying and then (iii) compression in order to give it sufficient mechanical strength essentially to prevent it from cracking when a gaseous fluid passes through it.

The compression ratio which is useful for the preparation of the pharmaceutical form is between about 1.1 and about 5, as indicated above. Advantageously, the said compression ratio will be between 1.2 and 4 and preferably between 1.25 and 3.60.

The microparticles of the active ingredient are coated so as to modify the conditions of disintegration of the said active ingredient in the organism, especially when administered orally. In particular, it makes it possible to mitigate so-called negative properties such as a bitter aftertaste, pronounced bitterness or excessively rapid solubilization of the active ingredient under normal conditions of administration. By forming an essentially continuous envelope, layer or film around the said microparticles, the coating also makes it possible to protect the active ingredient. This envelope can remain intact until it comes into contact with, or is in circulation in, a specific or appropriate body fluid. The coating can thus disappear by degradation or dissolution at a given point in the digestive tract so as to release the active ingredient, for example when it reaches the intestinal mucosa in the case of a stomach-resistant or acid-resistant coating. Finally, the coating can serve to promote the assimilation of the microparticles in the organism by means of a "mask" effect or a "liposome" effect, in a preferred embodiment of the invention, especially when the mean size of the particles which result from coating of the microparticles is of the order of a micrometer or preferably less.

For carrying out the method for the preparation of the pharmaceutical form according to the invention, the proportion of active ingredient in the solution or dispersion in water or the organic solvent of step (1°) is preferably less than or equal to 5% (w/v).

The purpose of the nebulization carried out in step (2°) is to obtain liquid microparticles of aerosol whose mean diameter is such that, after evaporation of the dissolving or dispersing solvent, solid microparticles are obtained which have a mean size of between 5 μm and 0.01 μm, preferably a mean size less than or equal to 2.5 μm and particularly preferably a mean size less than or equal to 1 μm.

The gaseous carrier fluid suitable according to the invention is a gas which is inert towards the active ingredient and the matrix formed by the filter element, for example nitrogen, argon and, if appropriate, dried air.

The evaporation of step (3°) is carried out at an appropriate temperature so as not to damage the active ingredient, especially at a temperature of between 25° and 90° C. Advantageously, the operation will be carried out at a temperature of between 30° and 65° C. If appropriate, it will be possible to use an increasing or decreasing temperature gradient.

The filtration of step (4°) is carried out with a pressure loss of between about 80 and about 10 000 Pa. The pressure loss, which depends particularly on the thickness of the filter element, its compression ratio (the ratio of the thickness of the material before compression to the thickness of the said material after compression) and the resulting porosity, as well as on the pressure of the gaseous fluid to be filtered, is generally between 1 cm of $H_2O$ (about 98.06 Pa) and 100 cm of $H_2O$ (about 9806 Pa), i.e. more precisely between 2 cm of $H_2O$ (about 196.1 pa) for an 8 mm thickness of filter material with a compression ratio of 1.25 and for a gaseous fluid with a flow rate of 300 l/min, relative to normal temperature and pressure conditions, and 76 cm of $H_2O$ (i.e. about 7452.5 Pa) for a 14 mm thickness of filter material with a compression ratio of 3.6 and for a gaseous fluid with a flow rate of 4 l/min, relative to normal temperature and pressure conditions.

After the filtration of step (4°), the method of the invention also comprises a so-called malaxation step (5°) to give a substantially homogeneous pharmaceutical form, in which step the filter element is intimately mixed with the microparticles which have been retained by the said filter element in step (4°). In fact, because of the mode of filtration, most of the retained microparticles are collected in the bulk of the filter element, in the vicinity of the inlet side of the said filter element which receives the gaseous fluid containing the solid microparticles to be collected.

In brief, in the said pharmaceutical form in the case of therapeutic and cosmetic active principles which are insoluble in water:

(A) the physiologically acceptable matrix is a porous solid material which has been obtained in the dry state by freezing, freeze-drying and compression in order to give the said material sufficient mechanically strength essentially to prevent it from cracking when a gaseous fluid passes through it; and (B) the active ingredient associated with the said matrix is insoluble in water and consists essentially of microparticles with a mean size of between 5 μm and 0.01 μm.

The method of preparation then comprises the following steps:

(1°) preparation of a solution of the said water-insoluble active ingredient in an organic solvent so that the concentration of the said active ingredient in the said solution is less than or equal to 10% (weight/volume);

(2°) nebulization of the said solution obtained in this way, in the form of a liquid aerosol entrained in a stream of gaseous carrier fluid;

(3°) evaporation of the solvent for the active ingredient in the said stream of gaseous carrier fluid so that the solid microparticles resulting from drying of the liquid microparticles of the aerosol are conveyed by the said gaseous carrier fluid; and (4°) filtration of the said gaseous carrier fluid containing the active ingredient essentially in the form of microparticles with a mean size of between 5 μm and 0.01 μm, on the one hand, and the solvent for the said active ingredient in the form of vapor, on the other, by means of a filter comprising, as the filter element, a solid, porous and water-soluble material which has been obtained in the dry state by freezing, freeze-drying and compression in order to give the said material sufficient mechanical strength essentially to prevent it from cracking when a gaseous fluid passes through it.

According to yet another aspect of the invention, a use of this method of preparation for collecting the microparticles of the water-insoluble active ingredient is proposed, whereby the matrix which is associated therewith and which has been used as the filter element during the filtration of step (4°) is dissolved in water.

In the pharmaceutical form in the case of therapeutic and cosmetic active principles which are soluble in water or coated:

(A) the physiologically acceptable matrix is a porous solid material which has been obtained in the dry state by freezing, freeze-drying and compression in order to give the said material sufficient mechanical strength essentially to prevent it from cracking when a gaseous fluid passes through it; and (B) the active ingredient associated with the said matrix consists essentially of microparticles with a mean size of between 5 μm and 0.01 μm and is selected from substances which are (1) soluble in water or (2) coated.

When the active ingredient is soluble in water, the method for the preparation of the pharmaceutical form comprises the following steps:

(1°) preparation of a solution of the said active ingredient in water so that the concentration of the said active ingredient in the said solution is less than or equal to 10% (w/v);

(2°) nebulization of the said solution obtained in this way, in the form of a liquid aerosol entrained in a stream of gaseous carrier fluid;

(3°) evaporation of the water, which is the solvent for the active ingredient, in the said stream of gaseous carrier fluid so that the solid microparticles resulting from drying of the liquid microparticles of the aerosol are conveyed by the said gaseous carrier fluid; and (4°) filtration of the said gaseous carrier fluid containing the active ingredient essentially in the form of microparticles with a mean size of between 5 μm and 0.01 μm, on the one hand, and the solvent for the said active ingredient in the form of vapor, on the other, by means of a filter comprising, as the filter element, a porous solid material which has been obtained in the dry state by freezing, freeze-drying and compression in order to give the said material sufficient mechanical strength essentially to prevent it from cracking when a gaseous fluid passes through it.

When the active ingredient is in the form of coated microparticles, the said method comprises the following steps:

(1°) preparation of a suspension of microparticles of the active ingredient in a liquid medium containing a dissolved coating material, the said active ingredient being insoluble in the said liquid medium and its concentration in the said liquid medium being less than or equal to 10% (w/v);

(2°) nebulization of the resulting suspension to give an aerosol entrained in a stream of gaseous carrier fluid;

(3°) evaporation of the liquid medium of the aerosol so that the coated microparticles which result from drying of the said aerosol are conveyed by the said gaseous carrier fluid; and (4°) filtration of the said gaseous carrier fluid containing the active ingredient essentially in the form of microparticles coated with the coating material, by means of a filter comprising, as the filter element, a porous solid material which has been obtained in the dry state by freezing, freeze-drying and compression in order to give the said material sufficient mechanical strength essentially to prevent it from cracking when a gaseous fluid passes through it for collection of the said coated microparticles on the filter element.

For the preparation of coated microparticles, the invention proposes a method which comprises:
nebulization of a solution of the active ingredient in water or an organic solvent;
drying of the resulting aerosol entrained in a gaseous carrier or vector fluid;
filtration of the said gaseous fluid by means of a filter element obtained by freezing, grinding, freeze-drying and then compression;
dissolution of the said filter element in a solvent in which the coating material is soluble, on the one hand, and in which the microparticles of the ingredient are insoluble, on the other;
nebulization of the resulting dispersion or suspension;
drying of the aerosol entrained in a gaseous carrier fluid, as indicated above; and
filtration on a filter element obtained by freezing, grinding, freeze-drying and then compression.

According to the best way of putting the invention into effect, the method for the preparation of coated microparticles comprises the following steps:

(a) preparation of a solution of the active ingredient in a first solvent so that the concentration of the said active ingredient in the said first solvent is less than or equal to 10% (w/v) and preferably less than or equal to 5% (w/v);

(b) nebulization of the said solution obtained in this way, in the form of a liquid aerosol entrained in a stream of gaseous carrier fluid;

(c) evaporation of the solvent for the active ingredient in the said stream of gaseous carrier fluid so that the solid microparticles resulting from drying of the liquid microparticles of the aerosol are conveyed by the said gaseous carrier fluid;

(d) filtration of the said gaseous carrier fluid containing the active ingredient essentially in the form of microparticles with a mean size of between 5 μm and 0.01 μm, on the one hand, and the solvent for the said active ingredient in the form of vapor, on the other, by means of a filter comprising, as the filter element, a porous solid material which has been obtained in the dry state by freezing, freeze-drying, grinding and compression in order to give the said material sufficient mechanical strength essentially to prevent it from cracking when a gaseous fluid passes through it;

(e) solubilization of the filter element used in step (d) in a second solvent in which (i) the active ingredient is insoluble and (ii) the coating material is soluble, so as to give a liquid medium consisting of the said second solvent, in which the coating material is dissolved and in which the microparticles to be coated are dispersed;

(f) nebulization of the resulting suspension to give an aerosol entrained in a stream of gaseous carrier fluid;

(g) evaporation of the solvent of the liquid medium in order to dry the aerosol, so that the coated microparticles which result from drying of the said aerosol are conveyed by the said gaseous carrier fluid; and (h) filtration of the said gaseous carrier fluid containing the coated particles of active ingredient, by means of a filter comprising, as the filter element, a porous solid material which has been obtained in the dry state by freezing, freeze-drying, grinding and compression in order to give the said material sufficient mechanical strength essentially to prevent it from cracking when a gaseous fluid passes through it.

The coating material suitable according to the invention is a film-forming organic substance which is soluble in a specific customary solvent and insoluble in the other, non-specific customary solvents. The coating material is generally of a polymeric nature. Particularly suitable coating materials are polymers and copolymers derived from acrylic acid, such as polyacrylic acids, polymethacrylic acids and the salts and esters thereof, cellulosic derivatives, glycerides, polyglycerides of fatty acids, lecithins, hydrogenated oils, polyoxyalkylene glycols such as polyoxyethylene glycols and polyoxypropylene glycols, polyacids such as polylactic and polygluconic acids, and mixtures thereof.

Generally suitable coating materials are waxes, fats and other physiologically acceptable coating means which are typically used or can be used in pharmacy, for example a 1/1 mixture by weight of ethyl cellulose (a product marketed under the trademark "AQUACOAT" by SEPPIC) and hydroxypropyl methyl cellulose (a product marketed under the name "PHARMACOAT 603" by SEPPIC).

Whether coated or not, the microparticles according to the invention can, if appropriate, be recovered by dissolution of the matrix which has been used as the filter element during the filtration of step (4°). The matrix is dissolved in an appropriate solvent in which the said coated or uncoated microparticles are insoluble.

Further advantages and characteristics of the invention will be understood more clearly from the following description of Examples and drawings, in which.

Of course, all these data are given by way of illustration and in no way imply a limitation.

Figures 1, 2:
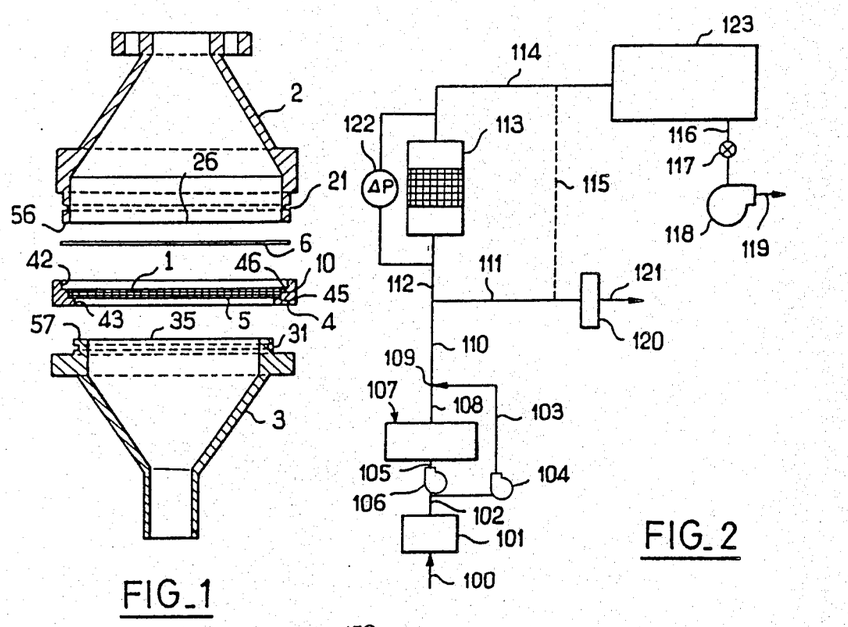
FIG. 1 schematically represents a view in section of a filter according to the invention, containing a lyophilized and compressed filter element.
FIG. 2 shows the diagram of an installation which makes it possible on the one hand to assess the efficacy of a filter and on the other hand to determine the particles conveyed by a gaseous fluid.
Figure 3:
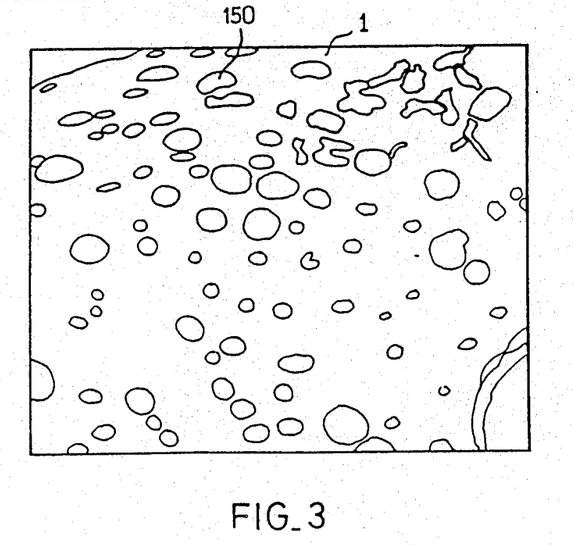
FIG. 3 is a reproduction of a photograph taken under a microscope, showing the submicron particles retained by the filter element according to the invention.

The best way of putting the invention into effect, as regards the preparation of the filter element and its efficacy, is shown in FIG. 1 and Examples 2-3.

According to FIG. 1, the filter according to the invention comprises a filter element 1 which is substantially perpendicular to the direction of a gaseous fluid to be filtered and is located between two ducts 2,3, parallel on the one hand to the outlet end 26 of the inlet duct 2 for the said fluid, and on the other hand to the inlet end 35 of the outlet duct 3 for the said fluid, in which filter the said filter element 1, which consists of a solid material obtained in the dry state and in a porous form by freezing, freeze-drying and then compression, is arranged between two perforated plates 5,6, especially grids, one of them, 6, being intended to fit onto the rim 56 of the end 26 of the said inlet duct 2, and the other, 5, being intended to fit onto the rim 57 of the end 35 of the said outlet duct 3, the said ducts 2,3 being designed on the one hand so that the said rims 56,57 cooperate like peripheral jaws, holding the said filter element 1 in place between the said perforated plates 5,6 housed between the said ends 26,35, and on the other hand so that the side edge 10 of the filter element 1 becomes impermeable to the said gaseous fluid at the time of use.

More precisely, this filter comprises three components: the inlet duct 2, the outlet duct 3 and the support 4 for the filter element 1, the said support being a disc arranged between the perforated plates 5 and 6, which here are advantageously grids whose mesh is very much larger than the diameter of the micron and submicron particles to be retained.

The upper grid 6 is intended to rest on the annular plate 46 of the support 4 and to come into contact with the rim 56 of the duct 2.

The lower grid 5 is intended to rest on the annular plate 45 of the support 4, on the one hand, and on the rim 57 of the duct 3, on the other.

As a means of lateral leaktightness, the ducts 2 and 3 each have a groove 21 and 31, respectively, in the vicinity of the ends 26 and 35, respectively, the said grooves each receiving an O-ring (not shown here); the side walls 42 and 43 of the support 4 come into intimate contact on the one hand with the corresponding outer side walls of the ducts 2 and 3, respectively, and on the other hand with the O-rings housed in the grooves 21 and 31, respectively, when the filter is assembled before being brought into service.

Furthermore, the ducts 2 and 3 can also have one or more means (not shown here) enabling them to be firmly fixed to one another.

EXAMPLE 1

An aqueous solution containing 7.5% by weight of Dextran 70 in water is prepared. The clarified solution is poured to a depth of 10 mm into cylindrical containers (Petri dish covers) of diameter 60 mm, the walls of which have been treated with silicone beforehand, and is then progressively frozen to $-50°$ C.

The frozen material is subsequently lyophilized under high vacuum (0.01 Torr, i.e. about 1.333 Pa) and then brought back to atmospheric pressure and room temperature by letting down the vacuum to a dry inert gas (nitrogen).

The resulting lyophilized material, which is then in the form of a very light but relatively strong cylindrical disc, is placed in the filter support 4 of a standard filtration unit of the type used by NILU (Norwegian Institute for Air Research, located in Oslo), which has been modified, as shown in FIG. 1, with grids 5 and 6 for holding the filter element 1, and grids 21 and 31 each provided with an O-ring.

The filter-holding apparatus is inserted in an analysis system between a sized particle generator, of the TSI type, Tri-Jet Aerosol Cenerator Model 3460, and a laser particle counter (PMS LAS-XCRT). A small circulating pump then sucks, through the filter, 40 ml/s of air containing a stable population of latex particles cf two dimensions—0.176 μm and 0.62 μm—originating from the generator.

The diagram of this system is illustrated in FIG. 2. Compressed air is injected at 100 and is filtered, according to a method known per se, by means of a conventional filter 101 fitted with a device making it possible to substantially to eliminate the water contained in the said compressed air, if necessary. The flow of dried filtered air 102 which leaves the filter 101 is divided into two streams: a diluting stream passing through the line 103 provided with a regulating pump 104, and a stream passing through the line 105 provided with a pump 106 and coming out into an aerosol generator 107. The stream charged with aerosol, 108, is diluted at 109 by the stream coming from the line 103. The resulting gaseous fluid follows the line 110 and again divides into two streams: a stream 111 directed towards a conventional filter 120 with a free outlet 121, or towards an optional branch 115 coming out into the line 114, and a stream directed by the line 112 towards a section 113 containing a filtration device according to the invention, as shown in FIG. 1. A branch provided with a manometer 122 is located opposite the section 113. The gaseous fluid filtered according to the invention is directed along the line 114 towards an optical particle counter 123 (especially a laser detector) and then along a line 116, provided with a flow monitoring device 117 and a pump 118, towards the outlet 119.

With a system of this type, the particle count in the exit air, integrated over periods of one minute, indicates that the particle capture rate is:

90% for the 0.62 micrometer size and
>95% for the 0.176 micrometer size.

These results, although very satisfactory for submicron particles, nevertheless indicate that filtration is not total. This can be explained by the fact that the lyophilized material based on pure Dextran lacks elasticity and that microcracks therefore appear in its bulk, both during drying and when it is placed under tension inside the filter holder by means of the O-rings.

EXAMPLE 2

An aqueous solution containing Dextran 70 (4%), Pharmacoat 603 (or hydroxypropyl methyl cellulose) (4%) and sucrose (0.0125%) is prepared. The clarified solution is poured to a depth of 10 mm into rectangular metal boxes which have been treated with silicone beforehand, and is then frozen at −50° C. as before.

At a temperature of −50° C., the frozen solution is released from the mold and the resulting plates are then ground in the cold by means of a hammer mill until homogeneous granules with a grain size of about 2 to 3 mm are obtained, which are then lyophilized as described above.

After they have been lyophilized and placed under an inert gas, the lyophilized granules are placed in a cylindrical filter holder closed at its lower part by a fine mesh resting on a circular diaphragm.

The lyophilized granules are then poured into the filter holder to a total height of 50 mm, or alternately 25 mm, and the whole is then placed on a support table making it possible to fit a cylindrical piston, which is set up at the top part of the filter holder. A controlled compression of the powder is then carried out until the total thickness has been reduced in a given ratio.

This operation produces a "sintered" lyophilized filter in the form of a very homogeneous and crack-free compact disc.

The filter and filter holder together are then placed in an apparatus analogous to that used for Example 1, between a source of sized particles (0.017–0.350–1.091 μm) and a laser detector 123 for detecting exit particles (FIG. 2). Air charged with an aerosol of latex particles is then injected continuously (4 liters/min) and the exit air is analyzed in order to evaluate the degree of filtration. The following Table gives the capture results for the different particle sizes as a function of the compression ratio. Efficacy of capture of microparticles by a lyophilized filter

| | | | | Pressure | Capture efficacy | | |
|---|---|---|---|---|---|---|---|
| | Thickness (cm) | Compression ratio | Density (g/cc) | loss (Pa) | $d_p = 1.091$ μm | $d_p = 0.350$ μm | $d_p = 0.107$ μm |
| Dextran 70 (4%) + | 1.96 | 2.6 | 0.10 | 3334 | 100.0 | 99.99 | 99.70 |
| Pharmacoat 603 (4%) + | 1.40 | 3.6 | 0.14 | 7452.5 | 100.0 | 99.99 | 99.93 |
| sucrose (0.0125%) | 1.27 | 2.0 | 0.08 | 2745.6 | 99.99 | 99.86 | 93.62 |

These results show that, by rational use of a more "plastic" lyophilized material compacted into a "sintered" filter by controlled compression, it is possible to produce a practically absolute filter retaining virtually all the finest particles in a gaseous stream carrying a submicron aerosol.

EXAMPLE 3

A compacted lyophilized filter is produced, as described above in Example 2, from an aqueous solution containing Dextran 70 (4%), Pharmacoat 603 (4%) and sucrose (0.0125%). The filter is placed on a support at the outlet for the stream of microparticles emitted by a generator of microparticles according to the invention, such as mentioned above. In the case of the present example, the microparticles are prepared from a solution containing 2.5% (w/v) of nifedipine [dimethyl 1,4-dihydro-2,6-dimethyl-4-(2-nitrophenyl)pyridine-3,5-dicarboxylate] in chloroform, which is injected into a stream of nitrogen in the nebulizers of a microparticle generator under a pressure of 4 bar, at a temperature of 25° C. and at a rate of 300 liters (NTP) of gas/min. The aerosol formed in this way is dried in the apparatus at a temperature of 30° C. and the microparticles formed are collected on a lyophilized filter identical to that described in Example 2, whose final thickness is 8 mm after slight compression of a 10 mm initial layer of granules.

Under these conditions, the pressure loss at the filter is insignificant (2 cm of water) and it is found that all the particles are trapped in the first three millimeters of the filter, which becomes yellow, and 4.5 grams of active product can be accumulated in the filter, in 10 minutes, for a total weight of filter material of 115 grams.

It then suffices to remove the filter and homogenize it to give a transformed intermediate starting material containing 3.9% of nifedipine in submicron form.

FIG. 3 schematically represents a photograph taken under a microscope (×10,000) after the filtration, according to the invention, of submicron particles of nifedipine in accordance with Example 3. The filter 1 comprises particles 150 of nifedipine on its surface. Under impact, the said particles visible on the surface of the filter 1 have partially penetrated the bulk of the material of the filter. In general, the particles 150 emerge from the said surface or are localized in the bulk, in the vicinity of the said surface, over a very small thickness.

According to the invention, a method for the preparation of a filter is proposed which comprises freeze-drying a liquid or pasty preparation of a polymeric substance and a solvating, diluting or dispersing liquid, the said freeze-drying comprising freezing at −40° C. to −80° C. followed by sublimation of the solvating, diluting or dispersing liquid, grinding the resulting solid product and then compressing the resulting ground product in a ratio of between 1.1 and 5.

According to the invention, a use of the filter 1 obtained by freeze-drying, grinding and compression is proposed for the purification and analysis of gaseous fluid. This use consists in passing the fluid to be purified or analyzed through a filter with a pressure loss of between 80 and 10,000 Pa.

Examples 4–6 which follow relate more particularly to the preparation of submicron particles of water-insoluble active principles.

EXAMPLE 4

A solution containing 2.5% (w/v) of nifedipine in chloroform is nebulized under a pressure of 4 bar in a carrier stream of dry nitrogen. The resulting aerosol is then dried at about 30° C. by circulation through a metal loop with an electrically heated wall. The aerosol of solid microparticles which is produced in this way is entrained towards a filter of low pressure loss and high efficacy, which has been prepared, as indicated in Example 2, by the controlled compression of lyophilized granules obtained from an aqueous composition containing 4% (w/v) of Dextran 70, 4% (w/v) of Pharmacoat 603 and 0.0125% (w/v) of sucrose. Under optimum use conditions, the filter retains all the microparticles which have been produced, while the gaseous carrier fluid, in this case nitrogen, which has been enriched with the vapors of evaporated chloroform and which comes out of the filter element, is directed towards a purification unit, for example a cryogenic condensation unit, enabling the solvent to be separated off before the gaseous carrier fluid is recycled.

At the end of the operation, the active ingredient used, in this case nifedipine, is entirely in the form of submicron particles "trapped" in the upper part of the lyophilized and compressed filter. The filter is then removed and homogenized to give a transformed industrial starting material rich in finely divided active product, which can be used as such, as a pharmaceutical form, or alternatively can be used as an intermediate in a series of other pharmaceutical operations.

EXAMPLE 5

700 g of a chloroform solution containing 2.5% (w/v) of nifedipine are nebulized in a carrier gas, namely dry nitrogen. The carrier gas is heated at a temperature of 30–35° C. for about 50 to 70 minutes so that the liquid microparticles are converted to solid microparticles by evaporation of the chloroform.

The microparticles of nifedipine are collected on 60 g of a filter, in the form of a disc, prepared as indicated in Example 4 above.

Analytical determination of the nifedipine shows the following:

(a) in the vicinity of the so-called inlet surface of the filter, there is 2.4% by weight of nifedipine;

(b) in the vicinity of the bottom (i.e. the outlet side) of the filter, there is 0.09% by weight of nifedipine; and (c) after homogenization, the mean content of nifedipine in the matrix is 0.58% by weight.

Furthermore, the content of residual solvent is less than 900 ppm (about 800–900 ppm) before homogenization and less than 400 ppm after homogenization.

The scanning electron micrographs show that the microparticles have a mean size of between 0.2 μm and 1 μm.

EXAMPLE 6

A compacted lyophilized filter is prepared, as described in Example 4 above, from an aqueous solution containing Dextran 70 (4%), Pharmacoat 603 (4%) and sucrose (0.0125%). The filter is placed on a support at the outlet for the stream of microparticles emitted by a microparticle generator. The microparticles are prepared from a solution containing 2.5% (w/v) of nifedipine in chloroform, which is injected into a stream of nitrogen in the nebulizers of a microparticle generator under a pressure of 4 bar, at a temperature of 25° C. and at a rate of 300 liters (NTP) of gas/min. The aerosol formed in this way is dried in the apparatus at a temperature of 30° C. and the solid microparticles formed are collected on a lyophilized and compacted filter whose final thickness is 8 mm after slight compression of a 10 mm initial layer of granules.

Under these conditions, the pressure loss at the filter is insignificant (about 196.1 Pa) and it is found that all the particles are trapped in the first three millimeters of the filter, which becomes yellow, and 4.5 grams of active product can be accumulated in the filter, in 10 minutes, for a total weight of filter material of 115 grams.

It then suffices to remove the filter and homogenize it to give an intermediate pharmaceutical form containing 3.9% of nifedipine in submicron form.

Examples 7–10 which follow illustrate the preparation of submicron particles of water-soluble active ingredients, on the one hand, and of submicron particles of coated active principles, on the other. They also illustrate the preparation of the novel pharmaceutical form according to the invention.

EXAMPLE 7

An aqueous solution containing 5% (w/v) of Buflomedil hydrochloride is prepared. 100 g of this solution are nebulized under a pressure of 3–4 bar in a stream of dry nitrogen. The resulting liquid aerosol is dried for 50 minutes under a temperature gradient of 44° C. (start of drying) to 50° C. (end of drying). The resulting microparticles are filtered on 45 g of a polyvinylpyrrolidone filter element obtained by freeze-drying and then compression.

Determination of the filter element makes it possible to observe that the amount of Buflomedil hydrochloride fixed to the filter is 4%.

The scanning electron micrographs show points of impact of the order of 0.1 μm to 0.2 μm, implying that it is possible to obtain particles with a size less than 0.1 μm.

EXAMPLE 8

The procedure, as indicated in Example 7 above, involves nebulizing 100 g of an aqueous solution containing 2% (w/v) of heparin, drying the resulting aerosol for 60 minutes with a temperature gradient of 60° C. (start of drying) to 50° C. (end of drying), and then collecting the resulting microparticles on 40 g of a freeze-dried and compressed polyvinylpyrrolidone filter.

Determination by flame photometry shows that the amount of sodium found on the filter corresponds to a fixation of the order of 1%, expressed as heparin sodium. The electron micrographs show uniform particles of the order of 0.1 to 0.5 μm, whereas the starting particles, when dissolved in water, were very heterogeneous and ranged from 10 to 100 μm or more.

EXAMPLE 9

The procedure indicated in Example 8 above is followed with an aqueous solution containing 5% (w/v) of heparin, i.e. a more concentrated solution than in Example 8.

Electron microscopic examination of a sample of the surface of the filter clearly confirms that the particles of heparin obtained are of the order of 0.1 to 0.5 μm.

EXAMPLE 10

The procedure, as indicated in example 8, involves nebulizing 400 g of an aqueous solution containing 5% (w/v) of heparin, which is collected on a polyvinylpyrrolidone (PVP) filter obtained, according to the invention, by freezing, grinding, freeze-drying and compression.

The filter is solubilized in 500 ml of chloroform and a composition of partial glycerides and polyglycerides of fatty acids, marketed under the trademark GELUCIRE, is then solubilized in the resulting mixture. The resulting suspension is nebulized and the coated microparticles are collected on a PVP filter according to the invention. The said coated microparticles of heparin obtained in this way have a mean size less than 1 μm; they can be associated, if appropriate, with microparticles of GELUCIRE.

What is claimed is:

1. A method of using a filter element to purify a gaseous fluid, which comprises the steps of (a) passing the gaseous fluid through the filter element with a pressure loss of between about 80 and 10,000 Pa, where in the filter element comprises a porous material produced by freeze-drying a liquid or paste to form a porous product and compressing the product in the form of a porous layer.

2. A filter element for gaseous fluid comprising a porous material produced by freeze-drying a liquid or paste to form a porous product and compressing the product in the form of a porous layer.

3. The filter element according to claim 2, wherein the product is compressed in order to give it sufficient mechanical strength essentially to prevent it from cracking when the gaseous fluid passes through it.

4. The filter element according to claim 2, wherein the product is compressed at a compression ratio of between about 1.1 and about 5.

5. The filter element according to claim 2, wherein the product is compressed at a compression ratio of between 1.25 and 3.60.

6. The filter element according to claim 2 wherein the porous material contains a plasticizing substances as a cohesive agent.

7. The filter element according to claim 6, wherein the cohesive agent is present in the solid material at a concentration of between 1% and 75% by weight, relative to the total weight of the solid material.

8. The filter element according to claim 2 wherein the porous material is soluble or dispersible in a solvent selected from the group consisting of water, non-aqueous inorganic solvents, organic solvents and mixtures thereof.

9. The filter element according to claim 2 wherein before freeze-drying, the liquid or paste has been frozen, then ground.

10. A filter comprising the filter element according to claim 2 disposed inside a frame support and sandwiched between two opposing perforated plates located between an inlet duct having an outlet end for the fluid and an outlet duct having an inlet end for the fluid, one of the perforated plates being intended to fit into a rim of the outlet end of the inlet duct, and the other perforated plate being intended to fit onto a rim of the inlet end of the outlet duct, the ducts being designed on the one hand so that the rims cooperate like peripheral jaws holding the filter element in place between the perforated plates housed between the inlet and outlet ends, and on the other hand so that the rims cooperate with the frame support to form a peripheral seal about the filter element.

11. A method for the preparation of a filter element comprising the steps of (a) freezing, at a temperature of −40° C. to −80° C., a liquid or pasty preparation of a polymeric substance and a solvating, diluting or dispersing liquid, (b) grinding the resulting frozen product, (c) freeze-drying the resulting ground product in order to sublime the solvating liquid, and then (e) compressing the resulting freeze-dried product at a ratio of between 1.1 and 5.

12. A pharmaceutical composition comprising a combination of (i) a physiologically acceptable matrix and (ii) at least one active ingredient in the form of particles, which is selected from therapeutic and cosmetic active principles, in which pharmaceutical composition:

(A) the physiologically acceptable matrix comprises a porous material produced by freezing a liquid or paste to a porous product and compressing the porous product at a ratio of between about 1.1 and 5 in order to give the material sufficient mechanical strength essentially to prevent it from cracking when a gaseous fluid passes through it; and (B) the active ingredient consists essentially of microparticles with a mean size of between 5 μm and 0.01 μm and is selected from the group consisting of substances which are (1) soluble in water, (2) insoluble in water, and (3) coated.

13. The pharmaceutical composition according to claim 12, wherein the porous material is produced by freeze-drying of an aqueous solution containing 4% (w/v) of dextran, 4% (w/v) of hydroxypropyl methyl cellulose and 0.0125% (w/v) of sucrose, followed by compressing a resulting lyophilizate at a ratio of between about 1.1 and about 5.

14. The pharmaceutical composition according to claim 12 wherein the porous material is produced by freeze-drying a solution containing polyvinyl-pyrrolidone, followed by compressing a resulting lyophilizate at a ratio of between about 1.1 and about 5.

15. A method for preparing a pharmaceutical composition according to claim 12, which comprises the following steps:
   (1°) production of a preparation of the active ingredient in a liquid medium at a concentration less than or equal to 10% (w/v);
   (2°) nebulization of the preparation to give an aerosol entrained in a stream of gaseous carrier fluid;
   (3°) evaporation of the liquid medium of the aerosol so that the microparticles which result from drying of the said aerosol are conveyed by the said gaseous carrier fluid; and
   (4°) filtration of the gaseous carrier fluid containing the microparticles through a filter element comprising the porous material.

16. A method for preparing the pharmaceutical composition of claim 12 wherein the active ingredient is insoluble in water, but soluble in an organic solvent, the method comprising the following steps:
   (1°) preparation of a solution of the water-insoluble active ingredient in an organic solvent so that the concentration of the active ingredient in the solution is less than or equal to 10% (w/v);
   (2°) nebulization of the solution to a liquid aerosol entrained in a stream of gaseous carrier fluid;
   (3°) evaporation of the organic solvent from the stream of gaseous carrier fluid to effect solid microparticles conveyed by the said gaseous carrier fluid and the organic solvent in the form of vapor; and
   (4°) filtration of the gaseous carrier fluid conveying the microparticles, and the organic solvent in the form of vapor through a filter element comprising the porous material.

17. The method according to claim 16 wherein the concentration of active ingredient in the solution is less than or equal to 5% (w/v).

18. The method according to claim 16 wherein liquid aerosol obtained by nebulization comprises aerosol particles whose mean diameter is such that, after evaporation of the solvent of the liquid preparation, solid microparticles are obtained which have a mean size of between 1 μm and 0.01 μm.

19. The method according to claim 16 wherein the evaporation of step (3°) is carried out at a temperature of between 25° and 90° C.

20. The method according to claim 16, which further comprises the step of malaxation of the filter element and the microparticles of active ingredient, which results from the filtration of step (4°).

21. The method according to claim 16 which further comprises collecting the microparticles of the active ingredient, by dissolving the porous material in a solvent in which the microparticles are insoluble.

22. A method for preparing the pharmaceutical composition of claim 12 wherein the active ingredient is soluble in water, the said method comprising the following steps:
   (1°) preparation of a solution of the active ingredient in water so that the concentration of the said active ingredient in the solution is less than or equal to 10% (w/v);
   (2°) nebulization of the solution to a liquid aerosol entrained in a stream of gaseous carrier fluid;
   (3°) evaporation of the water from the stream of gaseous carrier fluid to affect solid microparticles conveyed by the gaseous carrier fluid and water vapor; and
   (4°) filtration of the said gaseous carrier fluid containing the microparticles and the water vapor through a filter element comprising the porous material.

23. A method for preparing the pharmaceutical composition of claim 12 wherein the active ingredient is in the form of coated microparticles, the method comprising the following steps:
   (1°) preparation of a suspension of microparticles of the active ingredient in a liquid medium containing a dissolved coating material, the active ingredient being insoluble in the said liquid medium and its concentration in the said liquid medium being less than or equal to 10% (w/v);
   (2°) nebulization of the suspension to give an aerosol entrained in a stream of gaseous carrier fluid;
   (3°) evaporation of the liquid medium from the aerosol effecting coated microparticles conveyed by the gaseous carrier fluid; and
   (4°) filtration of the gaseous carrier fluid containing the coated microparticles through a filter element comprising the porous material.

24. The method according to claim 23, which further comprises the following steps:
   (a) solubilization of the filter element after the filtration step in a second solvent in which (i) the active ingredient is insoluble and (ii) the coating material is soluble, so as to give a liquid medium comprising the second solvent, in which the coating material is dissolved and in which the microparticles to be coated are dispersed;
   (b) nebulization of the liquid medium to give an aerosol entrained in a stream of gaseous carrier fluid;
   (c) evaporation of the solvent from the liquid medium in order to effect coated microparticles conveyed by the gaseous carrier fluid; and
   (d) filtration of the gaseous carrier fluid containing the coated microparticles through a filter element comprising the porous material.

* * * * *